United States Patent [19]
Fung et al.

[11] Patent Number: 5,489,610
[45] Date of Patent: * Feb. 6, 1996

[54] SUSTAINED RELEASE ORGANIC NITRITE THERAPY

[75] Inventors: Ho-Leung Fung, Getzville; John A. Bauer, Williamsville, both of N.Y.

[73] Assignee: Research Foundation of the State University of New York, Albany, N.Y.

[*] Notice: The portion of the term of this patent subsequent to Jan. 11, 2011, has been disclaimed.

[21] Appl. No.: 199,280

[22] PCT Filed: Jun. 30, 1993

[86] PCT No.: PCT/US93/06235

§ 371 Date: Mar. 1, 1994

§ 102(e) Date: Mar. 1, 1994

[87] PCT Pub. No.: WO94/01103

PCT Pub. Date: Jan. 20, 1994

Related U.S. Application Data

[63] Continuation-in-part of Ser. No. 908,224, Jul. 2, 1992, Pat. No. 5,278,192.

[51] Int. Cl.⁶ .................................................. A61K 31/13
[52] U.S. Cl. ........................... 514/506; 514/509; 514/645; 514/740

[58] Field of Search ....................... 514/506, 509, 514/645, 740

[56] References Cited

U.S. PATENT DOCUMENTS 5,278,192  1/1994  Fung et al. .............................. 514/645

OTHER PUBLICATIONS

Derwent Abstracts 78–35053A, "Medicaments for Treating Cardiogenic Shock", Fribolin et al. (1978).
Patent Abstracts of Japan, vol. 12, No. 467, Dec. 7, 1988, "Tape Preparation".

*Primary Examiner*—Frederick Krass
*Attorney, Agent, or Firm*—Kirschstein et al.

[57] ABSTRACT

A method of treating a patient suffering from a condition requiring vasodilator therapy, comprising long term, continuous adminstration of an organic nitrite to the patient in a dosage form capable of delivering a sufficient therapeutic amount of nitrite to the bloodstream of the patient thereby providing effective vasodilator therapy for at least 24 hours without the development of tolerance in the patient. The method of the invention is useful in treating conditions such as angina, particularly chronic, stable angina pectoris, ischemic diseases and congestive heart failure, and for controlling hypertension and/or impotence in male patients.

14 Claims, 4 Drawing Sheets

SUSTAINED RELEASE ORGANIC NITRITE THERAPY

CROSS-REFERENCE TO RELATED APPLICATION

This application is a continuation-in-part of Application Ser. No. 07/908,224, filed Jul. 2, 1992, now U.S. Pat. No. 5,278,192.

FIELD OF THE INVENTION

The present invention relates generally to drug therapy and, more particularly, to a method of vasodilator therapy for treating ischemic diseases, angina pectoris, hypertension and/or congestive heart failure.

BACKGROUND OF THE INVENTION

Congestive heart failure is a complex and heterogeneous disease state associated with decreased cardiac performance and increased pulmonary and peripheral oedema. Congestive heart failure results when the left, right or both ventricles fail to pump sufficient blood to meet the body's needs. An estimated 4 million people currently in the United States have congestive heart failure. While no single drug or drug class has proven to be ideal in treating this disease, vasodilator therapy constitutes a major approach in its clinical management.

Organic nitrate esters, such as nitroglycerin, isosorbide dinitrate, isosorbide-5-mononitrate, etc. are organic chemicals that contain the $ONO_2$ group. Nitrates are part of a family of vasodilators called nitrovasodilators and have enjoyed extensive use in cardiovascular therapy; but other members of this class, e.g., nitroprusside, molsidomine and organic nitrites are not organic nitrates. Nitrovasodilators such as isosorbide dinitrate and glyceryl trinitrate are useful in treating congestive heart failure because they cause a prompt reduction in preload and/or afterload, and relieve the venous congestion often associated with this disease.

Nitroglycerin, also referred to as trinitroglycerin or glycerin trinitrate, has also been used to treat angina pectoris for over 100 years. Nitroglycerin and other nitrovasodilators have been available for the treatment of angina pectoris and congestive heart failure in a number of different dosage forms for some time. These include sublingual, oral and buccal tablets as well as capsules, topical creams and ointments, patches, tapes, lingual sprays and intravenous solutions.

Transdermal nitroglycerin patches were introduced in recent years in an effort to overcome some of the disadvantages and inconveniences of other dosage forms. In particular, transdermal patches were formulated to provide increased systemic bioavailability as well as constant delivery of the drug over a 24 hour period or longer. Typically, the patches are applied once daily, either in the morning or evening, and changed daily at approximately the same time, and have become popular in the treatment of chronic, stable angina and congestive heart failure.

However, the positive effects of these patches are often short lived. For example, it has been shown that nitroglycerin produces rapid hemodynamic tolerance (within several hours) in congestive heart failure after continuous administration either by intravenous or transdermal routes. Intermittent dosing with a regimen of 12 hours on/12 hours off can avoid development of tolerance but the effect of the previous dose is lost within 2 hours of drug withdrawal, leaving the patient unprotected during the majority of the "dose-off" period. Furthermore, a more frequent on/off dosing strategy (4 or 8 hour on/off cycles) was not successful in avoiding tolerance development. At present no dosage regimen with nitrovasodilators has been developed that can achieve the dual objectives of avoidance of hemodynamic tolerance while continuously maintaining their beneficial effects.

Additionally, headaches typically accompany treatment with organic nitrates such as nitroglycerin. Headaches may be recurring with each daily dose, especially at higher doses. Aside from headaches, which may be severe and persistent, other adverse central nervous system (CNS) reactions include apprehension, restlessness, weakness, vertigo, dizziness and faintness.

SUMMARY OF THE INVENTION

The primary object of the present invention is to provide a new and improved method of vasodilator therapy, for example, in treating ischemic diseases, angina pectoris, congestive heart failure, impotence, and/or controlling hypertension, substantially without development of hemodynamic tolerance in the patient.

We have now discovered that tolerance associated with conventional vasodilator therapy (i.e., nitrovasodilators) can be avoided while providing effective long term, continuous treatment. More particularly, the present invention provides a method for treating a patient suffering from a condition requiring vasodilator therapy, comprising the long term, continuous administration of an organic nitrite to the patient in a dosage form capable of delivering a sufficient amount of the nitrite to the bloodstream to provide effective vasodilator therapy for at least 24 hours without development of tolerance in the patient. The method of the invention is useful in treating conditions such as, for example, angina, particularly chronic, stable angina pectoris, ischemic diseases and congestive heart failure, and for controlling hypertension and/or impotence in male patients.

In connection with the method of the invention, any conventional drug delivery system for the dosage form can be employed. It is understood that the drug delivery system can take virtually as many different forms as there are dosage forms available for delivery of nitrite to patients. For example, drug delivery systems within the scope of the invention include sublingual, oral and buccal tablets as well as capsules, caplets, tablets, topical creams and ointments, patches, tapes, lingual sprays and intravenous solutions.

DETAILED DESCRIPTION OF THE INVENTION

Figure 1:
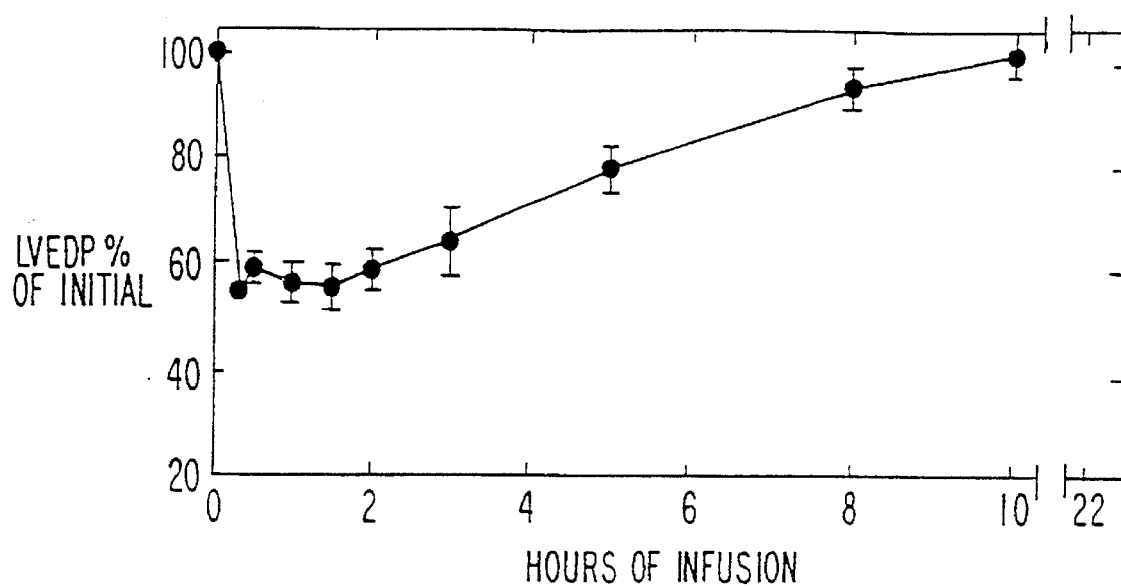
FIG. 1 is a graph illustrating the effects of continuous intravenous infusion (10–15 μg/min) of nitroglycerin to congestive heart failure rats. The pharmacologic effect measured was the left ventricular end-diastolic pressure (LVEDP).

The present invention provides a new vasodilator treatment for long term, continuous therapy, without the development of any significant degree of tolerance in the patient for at least one full day. More particularly, there is provided a method for long-term continuous administration of an organic nitrite for treatment of a patient suffering from a condition such as, for example, chronic angina pectoris, controlling blood pressure in hypertension and especially hypertension associated with surgical anesthesia and cardiovascular procedures, ischemic diseases, congestive heart failure or pulmonary edema associated with acute myocardial infarction and/or impotence in male patients. The organic nitrite can be administered in any known dosage form by any conventional route of administration, for example, lingually, sublingually, intrabuccally, orally, topically, by inhalation or by IV infusion or other parenteral modalities.

The only known clinical use of a nitrite for treating the above disease states is old, and includes the use of amyl nitrite for the acute relief of angina pectoris, not for long term, continuous drug therapy. Clinical use of amyl nitrite has never been found useful on a chronic basis. It is inconvenient, has a high incidence of adverse effects, has an unpleasant odor and is highly volatile.

For a better understanding of the present invention, it is first necessary to look at the tolerance problems associated with conventional nitrate therapy, the particular disease states to be treated and the biochemical mechanisms of organic nitrates and nitrites. Turning first to nitrate therapy, tolerance to the individual nitrates as well as cross-tolerance may occur with repeated, prolonged use.

Tolerance to the vascular and antianginal effects of the drugs has been shown in clinical studies, by experience from occupational exposure, and in isolated in vitro tissue experiments. Such tolerance is a principal factor limiting the efficacy of long-term nitrate therapy. Tolerance to nitrates appears to be associated with sustained plasma drug concentrations and frequent administration, i.e. continuous therapy. Rapid development of tolerance has occurred with oral, IV, and topical nitrate therapy (i.e., transdermal systems or nitroglycerin ointment). Tolerance to the pharmacologic effects is generally minor with intermittent use of sublingual nitrates. Furthermore, some evidence suggests that the development of tolerance can be prevented or minimized by use of an intermittent dosing schedule with a nitrate free interval of 10–12 hours (e.g., removal of a transdermal nitroglycerin system in the early evening and application of a new system the next morning, or other dosing regimens that allow for a nitrate-free period). Additionally, the intermittent closing schedule leaves the patient exposed to the potential risks of the condition during the "off" periods.

Adverse reactions to nitrate therapy, regardless of form of dosage, mainly involve the cardiovascular system. Headache, the most frequent adverse effect, may be severe (persistent or transient) and is perceived as a pulsating, throbbing sensation. Furthermore, postural hypotension may occur in patients receiving nitrates which may cause dizziness, weakness and other signs of cerebral ischemia. Some patients may have a marked sensitivity to the hypotensive effects of the nitrates and nausea, vomiting, weakness, restlessness, pallor, cold sweat, tachycardia, syncope and cardiovascular collapse may occur with therapeutic doses. In addition, in patients receiving transdermal delivery, peripheral edema rash and/or dermatitis may occur.

Turning to the various disease states which may be treated by the novel method, in one embodiment of the invention, nitrite therapy can be used in treating chronic, stable angina pectoris as well as unstable angina and silent ischemia. Angina pectoris is a symptom of myocardial ischemia that is usually secondary to coronary heart disease. "Angina pectoris" as used herein, means a sense of discomfort arising in the myocardium as a result of myocardial ischemia in the absence of infarction. Angina usually implies severe chest pain or discomfort. Coronary heart disease is the leading cause of death and disability in the United States and angina is the first clinical sign of this disease in about one-third of men and two-thirds of women. Patients who have a reproducible pattern of angina that is associated with a certain level of physical activity have chronic/stable angina. In contrast, patients with unstable angina are experiencing new angina or a change in their angina pattern, frequency or duration.

In another embodiment herein, nitrite therapy can be used for treating hypertension. Hypertension as used herein, is a cardiovascular disease characterized by elevation of blood pressure above arbitrary values considered "normal" for people of similar racial and environmental background. Hypertension affects the vasculature of all major organ systems (e.g., heart, brain, kidneys), and myocardial infarction and congestive heart failure (CHF) account for the majority of deaths secondary to hypertension (i.e., hypertension is a major etiologic factor in development of CHF). The morbidity and mortality that is associated with hypertension, increases linearly with higher systolic and diastolic blood pressures. The vast majority (e.g., about 85–90%) of individuals with hypertension have essential or primary hypertension which has no established cause. Hypertension is currently treated using thiazide diuretics, calcium channel blockers, beta blockers or angiotensin converting enzyme inhibitors, sometimes combined with non-drug interventions.

In still another embodiment of the invention, nitrite therapy can be used for treating congestive heart failure (CHF). CHF results when the left, right or both ventricles fail to pump sufficient blood to meet the body's needs. Increased cardiac workload and impaired myocardial contractility are important factors which contribute to the development of CHF. There are four major determinants which contribute to the left ventricular workload: preload, afterload, contractility and heart rate. Preload is the term to describe forces acting on the venous side of the circulation to affect myocardial wall tension. As venous return (i.e., blood flowing into the heart) increases, the volume of blood in the left ventricle increases. This increased volume raises the pressure within the ventricle (left ventricle end-diastolic pressure (LVEDP) which in turn increases the "stretch" or wall tension of the ventricle. An elevated preload will aggravate congestive heart failure. Afterload is the tension developed in the ventricular wall as contraction (systole) occurs. Afterload is regulated by the resistance or impedance against which the ventricle must pump during its ejection and is chiefly determined by arterial blood pressure. Contractility describes the inherent ability of the myocardium (cardiac muscle) to develop force and/or shorten independent of preload or afterload.

When the heart begins to fail, the body activates several complex compensatory mechanisms in an attempt to maintain cardiac output and oxygenation of vital organs. These include cardiac (ventricular) dilation, cardiac hypertrophy, increased sympathetic tone and sodium and water retention. Nitrate vasodilator therapy has been used to manage CHF unresponsive to the body's mechanisms and other traditional therapy, however, the problems associated with hemodynamic tolerance, as previously mentioned, and other adverse side effects render this therapy inadequate.

Organic nitrites which can be used in the present invention include any organic nitrite ester, i.e., any ester of nitrous acid and an organic alcohol, provided that the starting alcohol is not toxic and does not interfere with or counteract the vasodilating effect of the nitrite. Such organic nitrites can include, for example, straight or branched chain alkyl nitrites, arylalkyl nitrites, cycloalkyl nitrites, haloalkyl or halocycloalkyl nitrites and heterocyclic nitrites, as well as di- and trinitrite analogs of the foregoing. The di- and trinitrite esters may be produced by reacting nitrous acid with the appropriate diols or triols or by forming partial esters of polyols such as pentaerythritol. Preferred nitrites containing alkyl groups are those in which the alkyl is $C_1$–$C_{10}$.

Illustrative examples of organic nitrites which may be useful in the method of the invention are shown below.

| Structure | Formula | Name |
|---|---|---|
| (CH3)2CH-CH2-ONO | $C_4H_9NO_2$ | isobutyl nitrite |
| (CH3)2CH-CH2-CH2-ONO | $C_5H_{11}NO_2$ | isoamyl nitrite |
| ONO-CH2-CH2-CH2-ONO | $C_3H_6N_2O_4$ | 1,3-propane dinitrite |
| ONO-(CH2)7-ONO | $C_7H_{14}N_2O_4$ | 1,7-heptane dinitrite |
| CH3-CH2-CH(ONO)-CH2-CH3 | $C_6H_{13}NO_2$ | 3-hexyl nitrite |
| CH3-(CH2)6-CH2-ONO | $C_8H_{17}NO_2$ | octyl nitrite |
| (CH3)2CH-CH2-CH(ONO)-CH3 | $C_6H_{13}NO_2$ | 4-methyl-2-pentyl nitrite |
| (CH3)2CH-CH2-CH2-CH2-ONO | $C_6H_{13}NO_2$ | 4-methyl-1-pentyl nitrite |
| CH3-(CH2)4-CH(ONO)-CH3 | $C_7H_{15}NO_2$ | 2-heptyl nitrite |
| CH3-(CH2)4-CH(ONO)-CH2-CH3 | $C_8H_{17}NO_2$ | 3-octyl nitrite |
| CH3-CH2-CH2-C(ONO)(CH3)-CH3 | $C_6H_{13}NO_2$ | 2-methyl-2-pentyl nitrite |
| (CH3)2CH-CH2-CH2-CH(ONO)-CH3 | $C_7H_{15}NO_2$ | 5-methyl-2-hexyl nitrite |
| (CH3)2CH-(CH2)3-CH(ONO)-CH3 | $C_8H_{17}NO_2$ | 6-methyl-2-heptyl nitrite |

| Structure | Formula | Name |
|---|---|---|
| cyclohexyl-CH₂-ONO | C₇H₁₃NO₂ | cyclohexylmethyl nitrite |
| Ph-CH₂CH₂-ONO | C₈H₉NO₂ | 2-phenylethyl nitrite |
| ClCH₂-C(CH₃)₂-CH₂ONO | C₅H₁₀ClNO₂ | 3-chloro-2,2-dimethylpropyl nitrite |
| (CH₃)₃C-CH(ONO)-CH₃ (tert-amyl) | C₅H₁₁NO₂ | tert-amyl nitrite |
| (CH₃)(ONO)C(CH₃)-CH₂CH₂CH₂CH₃ | C₇H₁₅NO₂ | 2-methyl-2-hexyl nitrite |
| CH₃(CH₂)₅ONO | C₆H₁₃NO₂ | hexyl nitrite |
| ONO-CH₂-CH(CH₃)-CH₂-ONO | C₄H₈N₂O₄ | 2-methyl-1,3-propane dinitrite |
| ONO-CH₂-C(CH₃)₂-CH₂-ONO | C₅H₁₀N₂O₄ | 2,2-dimethyl-1,3-propane dinitrite |
| CH₃CH₂CH₂-C(CH₃)(CH₂ONO)₂ | C₇H₁₄N₂O₄ | 2-methyl-2-propyl-1,3-propane dinitrite |
| ONO-CH₂-CH(ONO)-CH₂-ONO | C₃H₅N₃O₆ | glyceryl trinitrite |
| RCH₂-CH(R')-R''  1-nitrite: R=ONO; R'=R''=OH or 2-nitrite: R=R''=OH; R'=ONO | C₃H₇NO₄ | glyceryl mononitrite |
| (isosorbide structure with HO and ONO) | C₆H₉NO₅ | isosorbide 5-mononitrite |
| (isoidide structure with HO and ONO) | C₆H₉NO₅ | isoidide 5-mononitrite |
| (isomannide structure with HO and ONO) | C₆H₉NO₅ | isomannide 5-mononitrite |
| HOCH₂-C(CH₂OH)(CH₂OH)-CH₂ONO | C₅H₁₁NO₅ | pentaerythrityl mononitrite |

-continued

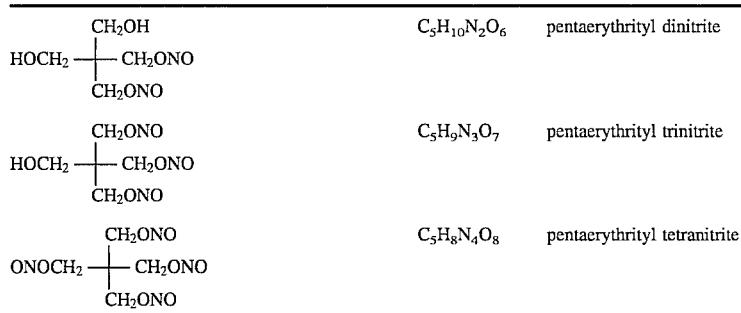

| | | |
|---|---|---|
| HOCH₂—C(CH₂OH)(CH₂ONO)—CH₂ONO | $C_5H_{10}N_2O_6$ | pentaerythrityl dinitrite |
| HOCH₂—C(CH₂ONO)(CH₂ONO)—CH₂ONO | $C_5H_9N_3O_7$ | pentaerythrityl trinitrite |
| ONOCH₂—C(CH₂ONO)(CH₂ONO)—CH₂ONO | $C_5H_8N_4O_8$ | pentaerythrityl tetranitrite |

In accordance with the present invention, the dosage of nitrite is preferably a daily dosage amount adequate to provide the necessary protection or relief to the patient from congestive heart failure, angina pectoris and/or hypertension symptoms. It is understood that the absolute amount will vary with the patient, the particular nitrite employed, and the dosage form to be administered. Also, these parameters will affect the delivery rates or fluxes employed in the drug delivery system utilized. For purpose of example only, various dosage forms are described hereinafter ill detail. However, it is apparent that the dosages will vary based on the above parameters.

In accordance with one embodiment of the invention, when a transdermal nitrite patch is employed, it is preferably applied at the same time each day to areas of clean, dry, hairless skin of the upper arm or body. Skin areas with irritation, extensive scarring or calluses should be avoided, and application sites should be rotated to avoid potential skin irritation. The usual initial adult dosage is 1 transdermal patch applied every 24 hours. The total nitrite delivered from a single patch (unit dosage) will be in the range of from about 1 to about 100 mg/day, preferably from about 2 to about 60 mg/day, and more preferably from about 5 to about 30 mg/day for the typical patient. It is understood theft transdermal nitrite drug delivery can be effected either through application of a gel or ointment (described hereinafter) to the skin or through the use of various commercially available transdermal delivery systems.

A number of different transdermal products which can employ the organic nitrite in accordance with the invention are described by Curtis Black, "Transdermal Drug Delivery", Pharmacist, Nov. 1982, pp. 49–75, which disclosure is hereby incorporated by reference. Additionally, exemplary patents relating to delivery systems include U.S. Pat. Nos. 4,191,015; 3,742,951; 4,191,015; 3,742,951 and 4,262,003 which disclose using a permeation enhancer to control delivery rates, which disclosures are hereby incorporated by reference.

The nitrite can also be applied topically as an ointment. The ointment is spread on any non-hairy skin area (usually the chest or back) in a thin, uniform layer without massaging or rubbing and using applicator paper typically supplied by the manufacturer. To protect clothing, plastic wrap held in place by an elastic bandage, tape or the like can be used to cover the ointment. The amount of nitrite reaching the circulation varies directly with the size of the area of application and the amount of ointment applied. The ointment is typically spread over an area approximately equivalent to 3.5 by 2.25 inches or greater (6 by 6 inches). A suggested initial dosage is 0.5 inch, squeezed from the tube, of the 2% ointment (approximately 7.5 mg) every 8 hours. When the dose to be applied is in multiples of whole inches, unit-dose preparations that provide the equivalent of 1 inch of the 2% ointment can be used. Dosages should be titrated upward until angina is effectively controlled or adverse effects preclude further increases. In the treatment of congestive heart failure (CHF), an initial dose of about 1.5 inches of 2% nitrite ointment (approximately 22.5 mg) can be used and gradually increased in 0.5 to 1-inch increments up to a dosage of 4 inches every 4–6 hours. Again, the dosage should be titrated upward until symptoms of CHF are controlled.

In accordance with another embodiment of the invention, the treatment is accomplished by an oral delivery system, the particular dosage form being selected from capsules, caplets, tablets and similar pharmaceutically acceptable oral dosage forms. When an oral dosage form is employed, the unit dose will be selected to deliver to the patient from about 2.5 to about 300 mg/day of nitrite, preferably from about 5 to about 160 mg/day, preferably, the entire daily unit dosage will be provided in one or two sustained release capsules, caplets or tablets designed to provide the desired drug delivery profile as described herein. Alternatively, combinations of different oral delivery dosage forms and strengths can be employed to achieve the desired drug delivery profile.

In accordance with still another embodiment of the invention, treatment of chronic, angina pectoris can be accomplished by sublingual and/or buccal dosages. For long-term treatment, nitrite extended-release buccal (transmucosal) tablets can be placed on the oral mucosa between the lip and gum above the upper incisors or between the cheek and gum. The tablet should be allowed to dissolve undisturbed. The initial dosage is preferably about 1 mg 3 times daily given every 5 hours during waking hours and dosage should be titrated upward incrementally until angina is effectually controlled. Preferably, for long-term treatment of angina pectoris, about 1.0 to 9.0 mg. of nitrite as an extended-release formulation can be administered orally about every 8 or 12 hours.

In accordance with still another embodiment of the invention, treatment of congestive heart failure can be accomplished by IV administration of nitrite. When administered by IV, the nitrite should be diluted with a suitable stabilizer before administration. The preferred dosage range for IV administration is about 5 µg/minute to about 500 µg/minute. It is recommended that IV administration begin with an initial low dosage, with the dosage to be titrated upward by increments of 5 or 10 µg/minute until the appropriate blood pressure response is obtained and/or chest pain decreases. The type of IV administration set used, polyvinyl chloride (PVC) or non-PVC, should be considered in dosage estimations.

The following examples are presented to further illustrate the method of the present invention and organic nitrite compounds which can be effectively used in practicing the method.

EXAMPLE I

Synthesis of Organic Nitrites

Certain organic nitrites and dinitrites useful in the present method of treatment were synthesized using an adaptation of the method of Bevillard and Choucroum, *Bull. Soc. Chim. France*, 337, 1957, whereby esterification of an alcohol or diol with nitrous acid produces a mononitrite or dinitrite ester.

A volume of 100 ml of distilled water was shaken with 100 ml of the parent alcohol in a separatory funnel at room temperature (23° C.). The water layer, now saturated with the alcohol, was separated and an aliquot of 40 ml was mixed with 4 grams of powder sodium nitrite. A volume of 0.5 ml of 4N HCl was added to the mixture dropwise over 3–5 minutes with constant stirring at 23° C., followed by the addition of 2 ml concentrated $H_2SO_4$ (also dropwise over 20 minutes). The mixture was stirred for 1 hour, and the nitrite formed separated as a layer on top of the aqueous mixture. This layer was separated at the end of the reaction, dried over $MgSO_4$, further purified by distillation if necessary, and stored at −20° C.

The existence of a nitrite product was indicated by the presence of a characteristic "fingerprint" in the ultraviolet absorbance spectrum between 300–400 nm. Gas chromatographic analysis indicated the presence of only one peak in the products. Identity of the specific nitrite was confirmed by elemental analysis.

EXAMPLE II

Rat Mode of Congestive Heart Failure

Congestive heart failure was produced in rats secondary to ligation of the left coronary artery, similar to the technique of Selye et al., "Simple Techniques for the Surgical Occlusion of Coronary Vessels in the Rat", Angiology, 1960, Vol. II, pp. 398–407, which disclosure is hereby incorporated by reference. Male Sprague-Dawley rats (300–325 grams) were anaesthetized with a combination of Innovar (0.3 ml $kg^{-1}$ intramuscularly, Pitman-Moore, Washington Crossing, N.J.) and diazepam (2.0 mg $kg^{-1}$ intramuscularly), then orally intubated and maintained by a Harvard rodent ventilator (Harvard Apparatus, South Natick, Mass.). A left thoracotomy was made at the fifth intercostal space, and the pericardium was gently torn. The left coronary artery was then ligated by an intramural suture (6–0 silk) placed just below the left atrium, approximately 3 mm from the origin. Vessel occlusion was ascertained by the paling of the ventricle distal to the suture. The lungs were then hyperinflated and the ribs closed by three interrupted sutures. The entire thoracotomy region was then swabbed with antibacterial ointment, and the muscle and skin layers were closed using an uninterrupted purse string suture. These animals were then allowed to recover for at least 6 weeks, producing a fully healed myocardial infarct. Complete occlusion of the left coronary artery in surviving rats typically produced a transmural infarct at the apex and anterior free wall of the left ventricle. Overall mortality of this procedure was approximately 40% during the 6–8 week recovery.

EXAMPLE III

Instrumentation

Rats were anaesthetized with halothane 1.5–2.0% in oxygen and maintained via a Harvard rodent ventilator. The right cartoid artery was isolated. A fluid filled (saline with 10 units $ml^{-1}$ heparin) length of polyethylene tubing (PE-50, Clay-Adams, Parsippany, N.J.) with a slightly tapered tip and no bevel was inserted and advanced to the left ventricle, approximately 2 mm past the aortic valve. The tapered tip was intended to minimize valvular damage during insertion. Proper placement of the catheter was assured by monitoring pressure waveforms detected by a Statham P231D pressure transducer (Gould, Cleveland, Ohio) and displayed on a Narco Biosystems Physiograph (Narco Biosystems, Houston, Tex.). The catheter was firmly secured and brought through a subcutaneous tunnel to the dorsal cervical region. The neck incision was then closed using a purse string suture.

To allow detachment of the transducer from the rat, so as to facilitate repeated haemodynamic measurements and instrument recalibration over many hours, a fluid filled needle hub/PRN adapter (Deseret Medical, Sandy, Utah) assembly was devised. This adapter was attached to the PE-50 catheter and securely sutured to the back of the neck. This system was similar in design and function to a marketed product developed for similar purposes by Vascular Assess Port, Norfolk Medical Products, Skokie, Ill. Left ventricular pressures were easily measured by penetrating the rubber septum of the PRN adapter assembly with a needle tipped length of PE-50 (fluid filled) which was connected to the transducer. No dampening of these pressure tracings occurred provided air bubbles were carefully avoided. Tracings using the needle hub/PRN adapter assembly were identical to the initial tracings made using a continuous length of tubing of comparable length (35–40 cm). Prior to recording ventricular pressures, the physiograph was properly calibrated using an identical needle hub/PRN adapter system and a pressure manometer placed at the approximate height of the animals head.

Determinations of left ventricular and diastolic and peak systolic pressures were carried out by calculating the mean of at least 30 consecutive tracings. Baseline haemodynamic measurements were made at least 3 hours after termination of halothane according to Flaim, et al., "Multiple Simultaneous Determinations of Haemodynamics and Flow Distribution in Conscious Rat", J. Pharmacol. Meth., 1984, Vol. II, pp. 1–39, which disclosure is hereby incorporated by reference, and their average values were calculated from at least 3 sets of tracings recorded over 30 minutes. This technique of left heart catheterization provided continuous measurement of stable left ventricular pressures typically for 1 day and often for as long as 2–3 days. Failure of the catheter system, when it occurred, was most commonly due to fouling of the tip within the left ventricle.

EXAMPLE IV

Nitroglycerin Infusion

Prior to left ventricular catheterisation, a polyethylene catheter (PE-50) was placed in the left femoral vein of the rat and tunneled subcutaneously to the base of the neck. Nitroglycerin (NTG) solution 1.0 mg/ml, Schwarz Pharma GmbH, Germany, was infused via this catheter using a Harvard infusion pump at a flow rate of 10–15 μg/min. Glass syringes were used for NTG infusion to avoid drug absorption. Rats with congestive failure (as previously described) were infused with NTG continuously for a period of 10 hours. Left ventricular pressures were measured in conscious, unrestrained rats periodically throughout the infusion experiment.

With reference to FIG. 1, the effects of continuous, long term infusion of NTG in congestive heart failure rats are shown. Pressure tracings were detected using high fidelity microtransducer and recorded by a Gould physiograph. The results show that intravenous infusion caused initial reduction in left ventricular end-diastolic pressure, but this effect is not maintained during continuous infusion for 10 hours, indicating the development of tolerance. Data is expressed as mean ± (SEM), n= 10–15.

EXAMPLE V

Isobutyl Nitrite Infusion

Infusion was carried out as described in Example IV except that the rats with congestive heart failure were infused with isobutyl nitrite (ISBN), instead of nitroglycerin, continuously for a period of 24 hours. Left ventricular pressures were measured in conscious, unrestrained rats periodically throughout the infusion experiment.

Figure 2:
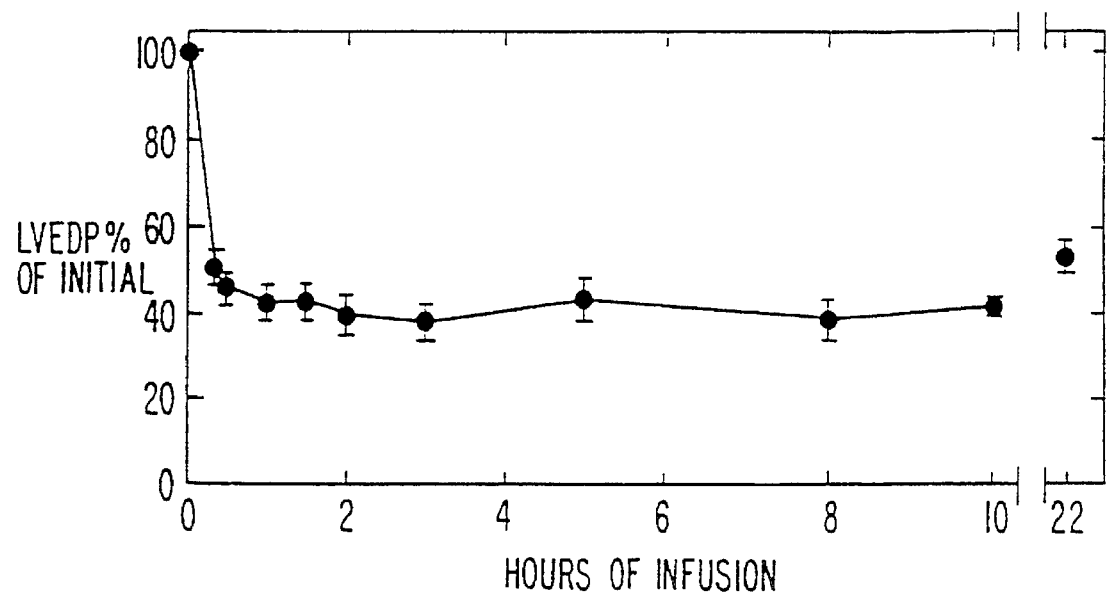
FIG. 2 is a graph illustrating the effects of continuous intravenous infusion (3.13 or 5.0 μl/hr) of isobutyl nitrite to congestive heart failure rats. The pharmacologic effect measured was the LVEDP.

With reference to FIG. 2, the effects of continuous, long term infusion of ISBN to congestive heart failure rats; are shown. Intravenous infusion (3.13 or 5.0 µl/hr) caused rapid initial reductions in left ventricular end-diastolic pressure, and these initial effects were maintained throughout the infusion period, most significantly, even after 24 hours of continuous infusion. These results demonstrate that ISBN can be a useful and novel vasodilator, without tolerance development within the first 24 hours as was seen after just about 2 hours for infusion with nitroglycerin (FIG. 1).

EXAMPLE VI

Transdermal Administration

A 2% ointment of isobutyl nitrite (ISBN) in petrolatum was prepared. Approximately 500 mg of the ointment was then applied to the shaved abdomen of an anesthetized rat. Arterial blood pressure and heart rate was measured in the rat before and during ointment application. It was observed that ointment application caused a reduction in blood pressure after 35 minutes of ointment application. The average blood pressure over 30 minutes prior to ointment treatment was 108/83 mmHg. At 35–40 minutes after application, blood pressure was 93/68 mmHg. These results suggest that ISBN is capable of being absorbed transdermally at concentrations significant to produce a vasodilator effect and they are consistent with the high lipophilicity of ISBN.

EXAMPLE VII

Isoamyl Nitrite Infusion

Infusion was carried out as described in Example IV, except that the rats with congestive heart failure were infused with isoamyl nitrite, instead of nitroglycerin, continuously for a period of 24 hours. Left ventricular pressures were measured in conscious, unrestrained rats periodically throughout the infusion experiment.

Figure 3:
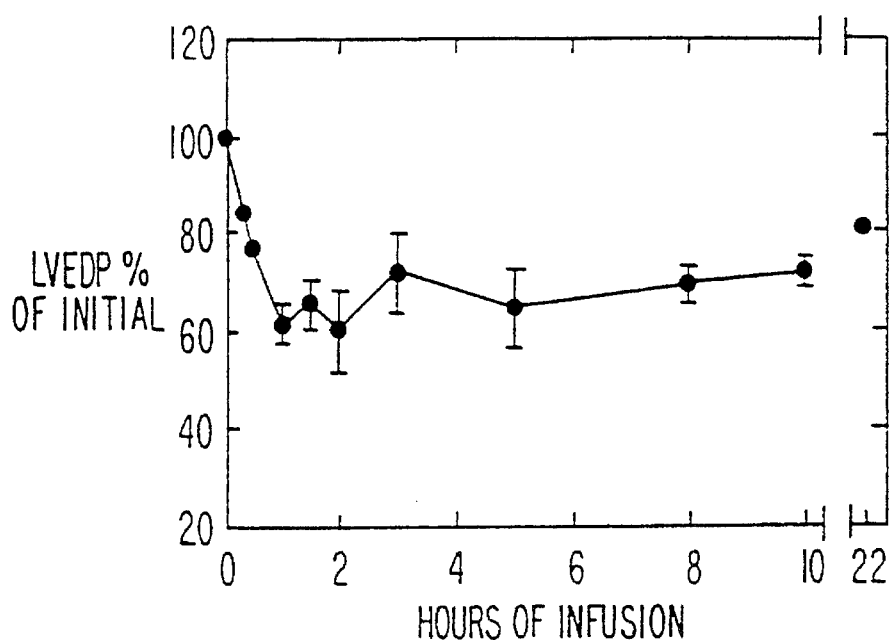
FIG. 3 is a graph illustrating the effects of continuous intravenous infusion (3.13 μl/hr) of isoamyl nitrite to congestive heart failure rats. The pharmacologic effect measured was the LVEDP.

With reference to FIG. 3, the effects of continuous, long term infusion of isoamyl nitrite to congestive heart failure rats are shown. Intravenous infusion (3.13 µl/hr) caused rapid initial reductions in left ventricular end-diastolic pressure, and these initial effects were maintained throughout the infusion period, most significantly, even after 24 hours of continuous infusion. These results demonstrate that isoamyl nitrite can be a useful and novel vasodilator, without tolerance development within the first 24 hours as was seen after just about 2 hours for infusion with nitroglycerin (FIG. 1).

EXAMPLE VIII–XII

Figure 4:
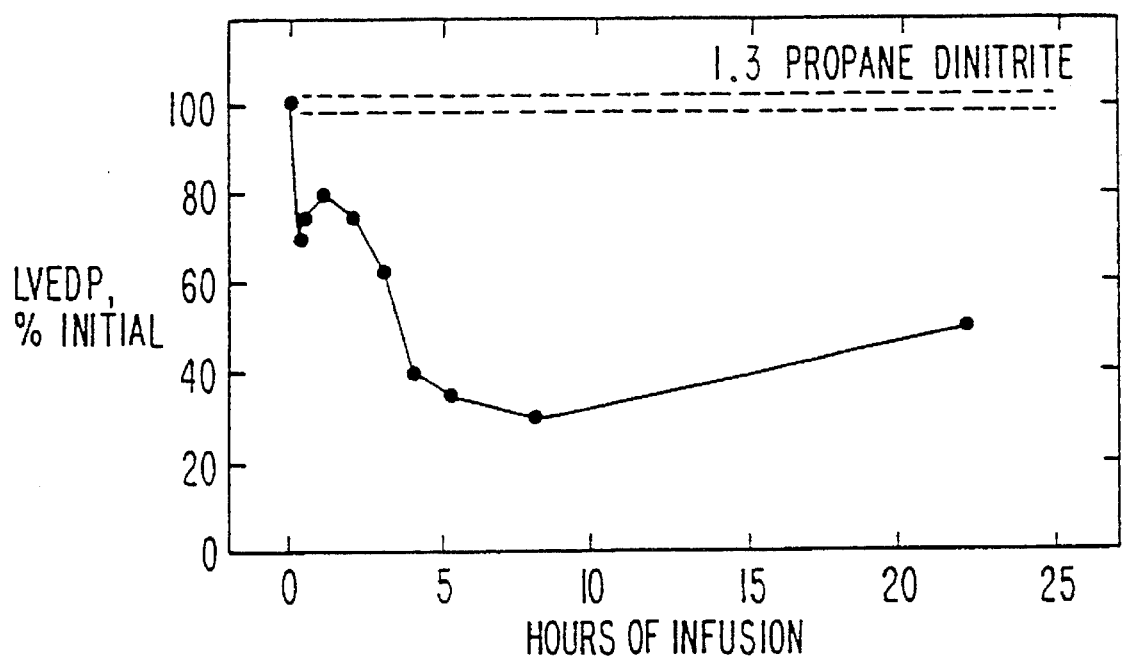
FIG. 4 is a graph illustrating the effects of continuous intravenous infusion (1.0 μl/hr) of 1,3-propane dinitrite to FIG. 5 is a graph illustrating the effects of continuous intravenous infusion (1.0 µl/hr) of 1,7-heptane dinitrite to congestive heart failure rats. The pharmacologic effect measured was the LVEDP.
Figure 5:
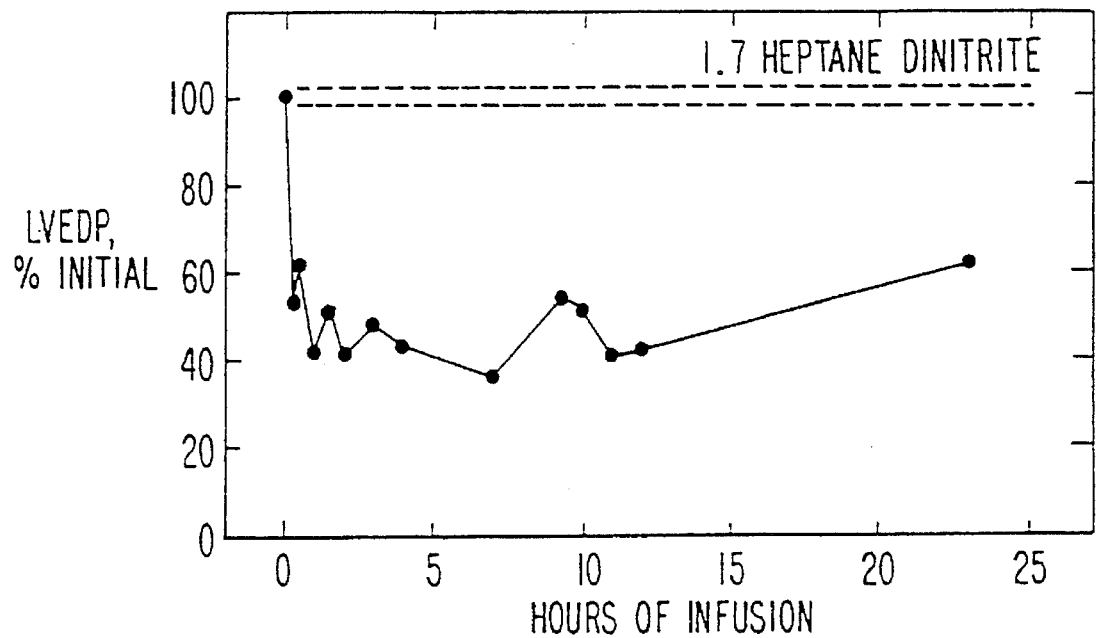
Figure 6:
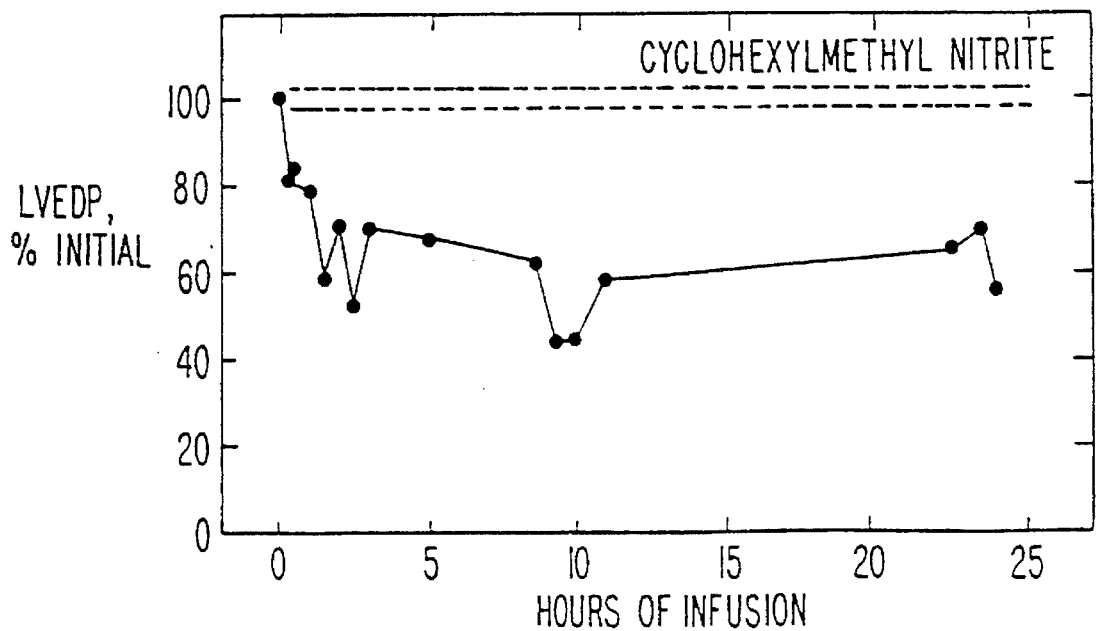
FIG. 6 is a graph illustrating the effects of continuous intravenous infusion (3.13 µl/hr) of cyclohexylmethyl nitrite to congestive heart failure rats. The pharmacologic effect measured was the LVEDP.
Figure 7:
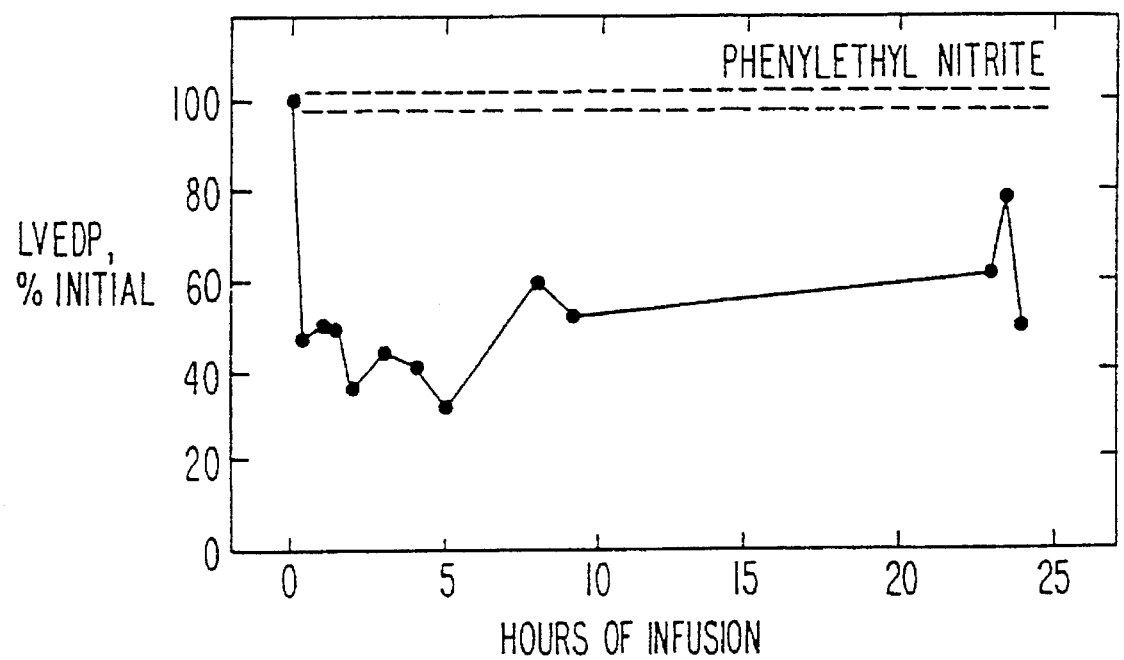
FIG. 7 is a graph illustrating the effects of continuous intravenous infusion (3.13 µl/hr) of phenylethyl nitrite to congestive heart failure rats. The pharmacologic effect measured was the LVEDP.
Figure 8:
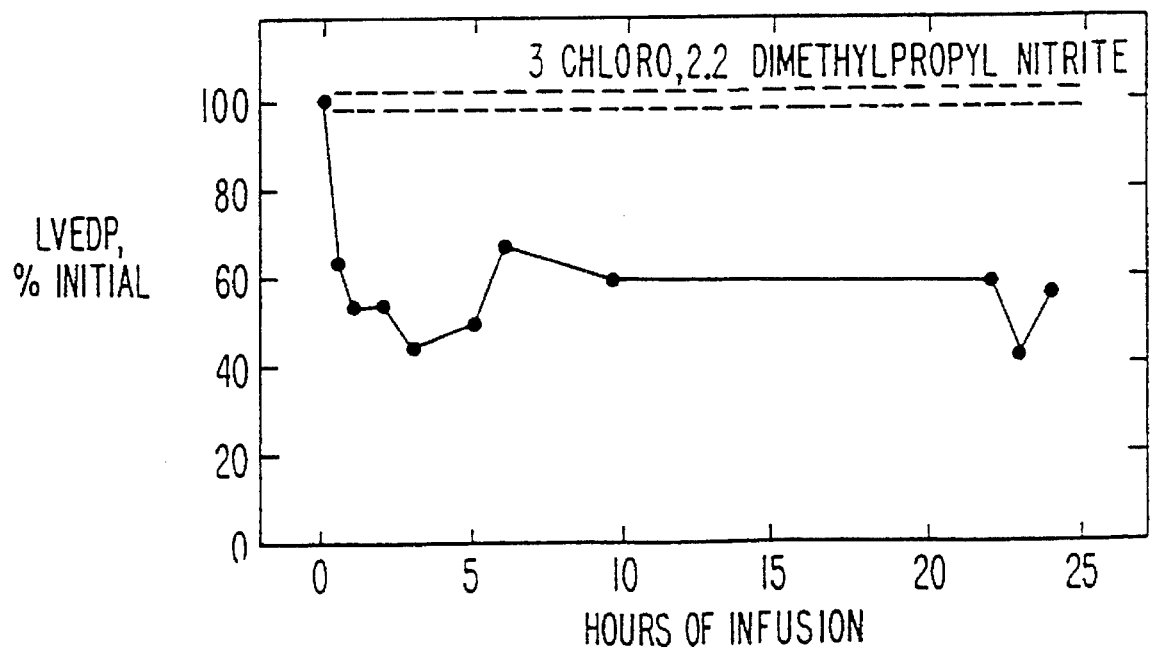
FIG. 8 is a graph illustrating the effects of continuous intravenous infusion (3.13 µl/hr) of 3-chloro- 2,2-dimethylpropyl nitrite to congestive heart failure rats. The pharmacologic effect measured was the LVEDP.

Infusion was carried out as described in Example IV except that the rats with congestive heart failure were infused with the nitrites listed below. The infusion rate was 1.0 µl/hr for Examples VIII and IX and 3.13 µl/hr for Examples X, XI and XII. The results of each infusion are reflected in the respective figures indicated:

| Example | Nitrite | Results Shown In |
| --- | --- | --- |
| VIII | 1,3-propane dinitrite | FIG. 4 |
| IX | 1,7-heptane dinitrite | FIG. 5 |
| X | cyclohexylmethyl nitrite | FIG. 6 |
| XI | Phenylethyl nitrite | FIG. 7 |
| XII | 3-chloro-2,2-dimethyl-propyl nitrite | FIG. 8 |

In each instance the initial rapid reductions in LVEDP were substantially maintained even after 24 hours of continuous infusion.

EXAMPLE XIII

Effect of Nitrite Therapy on the Central Nervous System

It was observed that during nitrite therapy there was a lack of apparent effects on the central nervous system of the rats. During nitroglycerin infusion, the rats invariably became lethargic and they would not eat, drink or move about in their cages. These behaviors, which disappeared rapidly after the drug was withdrawn, likely are reflective of the known side-effects of nitroglycerin, i.e., the occurrence of headache in patients. When rats with heart failure were infused with nitrites, at doses which produced comparable hemodynamic effects as nitroglycerin, the rats appeared normal and carried out their routine activities. These observations suggest that nitrites may not cause the undesirable effects on the central nervous system that are produced by nitroglycerin and other nitrates.

It should be understood that the Examples described herein are for purposes of illustration only and not limitation, and that various modifications and/or changes that may suggest themselves to one skilled in the art are intended to be included within the spirit of this application and the scope of the appended claims.

We claim:

1. A method of vasodilator therapy for treating a patient suffering from a condition requiring such therapy, comprising the long-term, continuous administration of an organic nitrite to the patient in a dosage form capable of delivering a sufficient therapeutic amount of said nitrite to the bloodstream of the patient, thereby providing effective vasodilator therapy for at least 24 hours without development of tolerance in the patient, said nitrite being selected from the group consisting of 1,3-propane dinitrite, 1,7-heptane dinitrite, cyclohexylmethyl nitrite, 2-phenylethyl nitrite, 3-chloro-2,2 dimethylpropyl nitrite, tert-amyl nitrite, 2-methyl-2-hexyl nitrite, hexyl nitrite, 2-methyl-1,3-propane dinitrite, 2,2, dimethyl-1,3-propane dinitrite, 2-methyl-2-propyl- 1,3-propane dinitrite, 3-hexyl nitrite, octyl nitrite, 4-methyl-2-pentyl nitrite, 4-methyl- 1-pentyl nitrite, 2-heptyl nitrite, 3-octyl nitrite, 2-methyl- 2-pentyl nitrite, 5-methyl-2-hexyl nitrite, 6-methyl-2-heptyl nitrite, glyceryl dinitrite, glyceryl mononitrite, isosorbide 5-mononitrite, isoidide 5-mononitrite, isomannide 5-mononitrite, pentaerythrityl mononitrite, pentaerythrityl dinitrite, pentaerythrityl trinitrite and pentaerythrityl tetranitrite.

2. The method of claim 1, wherein said dosage form is a transdermal delivery system.

3. The method of claim 2, wherein said transdermal delivery system is selected from the group consisting of a patch, tape, ointment and topical cream.

4. The method of claim 1, wherein said dosage form is an intravenous infusion.

5. The method of claim 1, wherein said nitrite is administered by a route selected from the group consisting of sublingual, oral and buccal.

6. The method of claim 5, wherein said dosage form is a tablet, capsule or caplet.

7. The method of claim 3, wherein said transdermal system is a patch.

8. The method of claim 7, wherein the dosage of nitrite administered to the patient from said patch is at least 2 mg/day.

9. The method of claim 8, wherein the dosage of nitrite administered to the patient from said patch is between 5 and 100 mg/day.

10. The method of claim 1, wherein said nitrite is selected from the group consisting of 1,3-propane dinitrite, 1,7-heptane dinitrite, cyclohexylmethyl nitrite, 2-phenylethyl nitrite and 3-chloro-2,2 dimethylpropyl nitrite.

11. The method of claim 1, wherein said condition is selected from the group consisting of angina pectoris, congestive heart failure, hypertension, ischemic disease, impotence and unstable angina.

12. The method of claim 11, wherein said condition is angina pectoris.

13. The method of claim 1, wherein said condition is congestive heart failure.

14. The method of claim 1, wherein said dosage is delivered to the patient at a constant rate.

* * * * *